(12) United States Patent
Kondo et al.

(10) Patent No.: US 7,837,935 B2
(45) Date of Patent: Nov. 23, 2010

(54) JOINT FOR JOINING HYDROGEN GAS RUNNING ROUTE-FORMING MEMBERS AND PORTABLE HYDROGEN FLAME IONIZATION GAS DETECTOR

(75) Inventors: Haruhiko Kondo, Tokyo (JP); Nobuhisa Kawai, Tokyo (JP); Yukio Nakamura, Tokyo (JP)

(73) Assignee: Riken Keiki Co., Ltd., Tokyo (JP)

( * ) Notice: Subject to any disclaimer, the term of this patent is extended or adjusted under 35 U.S.C. 154(b) by 1274 days.

(21) Appl. No.: 11/391,914

(22) Filed: Mar. 29, 2006

(65) Prior Publication Data

US 2006/0228266 A1 Oct. 12, 2006

(30) Foreign Application Priority Data

Apr. 11, 2005 (JP) ............................. 2005-113417

(51) Int. Cl.
*G01N 33/00* (2006.01)
(52) U.S. Cl. .............................. 422/54; 422/83; 422/94
(58) Field of Classification Search ................... 422/54, 422/83, 94
See application file for complete search history.

(56) References Cited

U.S. PATENT DOCUMENTS 4,211,746 A * 7/1980 Mees ........................... 422/54

FOREIGN PATENT DOCUMENTS

JP 2000-227416 A 8/2000

* cited by examiner

*Primary Examiner*—Sam P Siefke
(74) *Attorney, Agent, or Firm*—Holtz, Holtz, Goodman & Chick, PC

(57) ABSTRACT

Disclosed is a small-sized joint for joining hydrogen gas running route-forming members, which can surely prevent the leakage of hydrogen gas, and a portable hydrogen flame ionization gas detector that can prevent the leakage of hydrogen gas to achieve high safety.

The joint comprises a metallic base having an internal space at least one end of which is opened, and a ring-like sealing member composed of an elastic material and arranged at opening edge of the metallic base, wherein a hydrogen gas running route-forming member is fixed in a state inserted into an internal space of the metallic base through the sealing member, and the sealing member is squeezed to gastightly seal the space, whereby one hydrogen gas running route-forming member is removably joined. In the gas detector, the joint is used to form a hydrogen gas running route.

12 Claims, 3 Drawing Sheets

JOINT FOR JOINING HYDROGEN GAS RUNNING ROUTE-FORMING MEMBERS AND PORTABLE HYDROGEN FLAME IONIZATION GAS DETECTOR

BACKGROUND OF THE INVENTION

1. Field of the Invention

The present invention relates to a joint for joining hydrogen gas running route-forming members and a portable hydrogen flame ionization gas detector, in which a hydrogen gas running route is formed by means of this joint for joining hydrogen gas running route-forming members.

2. Description of the Background Art

As a method for detecting a concentration of, for example, a hydrocarbon gas, has heretofore been used, for example, a system that gaseous molecules of the hydrocarbon gas are ionized in a hydrogen flame to detect an ionic current, and the concentration of the hydrocarbon gas is detected on the basis of the result of the detection of the ionic current.

As hydrogen flame ionization gas detectors making good use of such a detection system, have been proposed those of various structures (see, for example, Japanese Patent Application Laid-Open No. 2000-227416), and portable gas detectors are used in tests for gas leakage from, for example, conduits and supply pipes buried in the ground.

In a portable hydrogen flame ionization gas detector, it is necessary to arrange all necessary component members within a limited space in a case for the detector making up the hydrogen flame ionization gas detector, and it is thus substantially difficult to form a whole hydrogen gas running route from a hydrogen gas supply source to a sensor part by one pipe member. Accordingly, under the circumstances, a plurality of hydrogen gas running route-forming members are joined with a joint or joints to arrange a pipeline, thereby forming a hydrogen gas running route.

However, the joint used in the formation of the hydrogen gas running route desirably has a structure that at least one hydrogen gas running route-forming member is removably joined to the joint from the reasons of, for example, the necessity of maintenance.

As such a joining method is generally often used, for example, a method in which a gas running route-forming member is screwed into a joint. Since the atom of hydrogen gas is extremely small, however, the hydrogen gas may be leaked from the joined portion by the screwing when hydrogen gas runs. As a result, there is a risk of causing firing, explosion or the like.

In order to solve such a problem, a measure for preventing the leakage of the hydrogen gas from the joined portion has been taken in conventional joints for joining hydrogen gas running route-forming members.

However, such a joint is generally liable to become large in size and hence hard to use for forming a hydrogen gas running route in a portable hydrogen flame ionization gas detector and involves a possibility that the whole gas detector may become enlarged.

SUMMARY OF THE INVENTION

The present invention has been made on the basis of the foregoing circumstances and has as its object the provision of a joint for joining hydrogen gas running route-forming members, which can be fabricated in a sufficiently small size though the leakage of hydrogen gas is surely prevented.

Another object of the present invention is to provide a portable hydrogen flame ionization gas detector that can be fabricated with a small occupation space for a hydrogen gas running route in a case for the detector and the leakage of hydrogen gas is prevented to achieve high safety.

According to the present invention, there is thus provided a joint for joining hydrogen gas running route-forming members, at least one of which is joined removably thereto, the joint comprising:

a metallic base having an internal space for forming a space for ejection of hydrogen gas, at least one end of which is opened, and a ring-like sealing member composed of an elastic material and arranged at opening edge of the metallic base, wherein one hydrogen gas running route-forming member removably joined is fixed in a state inserted into a central through-hole of the sealing member and the internal space in such a manner that a hydrogen gas ejecting opening is located within the space for ejection of hydrogen gas formed with the internal space, and the sealing member is squeezed, whereby the juncture of said one hydrogen gas running route-forming member is achieved; and wherein another hydrogen gas running route-forming member is joined to open into the space for ejection of hydrogen gas.

In the joint according to the present invention for joining hydrogen gas running route-forming members, the joint may be so constructed that said one hydrogen gas running route-forming member is joined in a state brought into no contact with an inner wall of the internal space in the metallic base.

In the joint according to the present invention for joining hydrogen gas running route-forming members, the joint may also be so constructed the metallic base is cylindrical, and sealing members are arranged at opening edges located at both ends of the metallic base, wherein said one hydrogen gas running route-forming member is composed of a large-diameter rod portion and a small-diameter rod portion continuing to an end of the large-diameter rod portion, in which a gas conduit with a gas ejecting opening opened through a peripheral wall of the small-diameter rod portion is formed, and wherein said one hydrogen gas running route-forming member is inserted and arranged into the internal space for forming the space for ejection of hydrogen gas of the metallic base in a state that a tip portion of the small-diameter rod portion is projected outside, and a fastening member is screwed on the tip portion, whereby said one hydrogen gas running route-forming member is fixed in a state that the sealing members have been squeezed.

In the joint according to the present invention for joining hydrogen gas running route-forming members, the joint may further be so constructed that the another hydrogen gas running route-forming member is integrally fixed and joined to the metallic base, and that the another hydrogen gas running route-forming member is fixed through a peripheral wall of the metallic base.

According to the present invention, there is also provided a portable hydrogen flame ionization gas detector making use of a joint for joining hydrogen gas running route-forming members to form a hydrogen gas running route, wherein the joint for joining hydrogen gas running route-forming members at least one of which is joined removably thereto and comprises:

a metallic base having an internal space for forming a space for ejection of hydrogen gas, at least one end of which is opened, and a ring-like sealing member composed of an elastic material and arranged at opening edge of the metallic base, and wherein one hydrogen gas running route-forming member removably joined is fixed in a state inserted into a central through-hole of the sealing member and the internal space in such a manner that a hydrogen gas ejecting opening is located within the space for ejection of hydrogen gas formed with the internal space, and the sealing member is squeezed, whereby said one hydrogen gas running route-forming member is joined to the joint and another hydrogen gas running route-forming member is joined to open into the space for ejection of hydrogen gas.

In the portable hydrogen flame ionization gas detector according to the present invention, the detector may also be so constructed that the metallic base is cylindrical, and sealing members are arranged at opening edges located at both ends of the metallic base, wherein said one hydrogen gas running route-forming member is composed of a large-diameter rod portion and a small-diameter rod portion continuing to an end of the large-diameter rod portion, in which a gas conduit with a gas ejecting opening opened through a peripheral wall of the small-diameter rod portion is formed, and wherein said one hydrogen gas running route-forming member is inserted and arranged into the internal space for forming the space for ejection of hydrogen gas of the metallic base in a state that a tip portion of the small-diameter rod portion is projected outside, and a fastening member is screwed on the tip portion, whereby said one hydrogen gas running route-forming member is fixed in a state that the sealing members have been squeezed.

In the portable hydrogen flame ionization gas detector according to the present invention, the detector may further be so constructed that the another hydrogen gas running route-forming member is integrally fixed and joined to the metallic base, and that the another hydrogen gas running route-forming member is fixed through a peripheral wall of the metallic base.

According to the joint (hereinafter referred to as "joint" merely) according to the present invention for joining hydrogen gas running route-forming members, one hydrogen gas running route-forming member removably joined is fixed in a state brought into no direct contact with the inner wall forming the space for ejection of hydrogen gas in the metallic base, and said one hydrogen gas running route-forming member is gastightly sealed by the sealing member to the metallic base at the opening edge of the space for ejection of hydrogen gas, whereby the juncture of said one hydrogen gas running route-forming member is achieved, so that hydrogen gas can be surely prevented from leaking from the joined portion. In addition, the joint has an extremely simple structure that the sealing member is arranged at the opening edge of the metallic base, so that the joint itself can be fabricated in a sufficiently small size.

According to the portable hydrogen flame ionization gas detector of the present invention, which makes good use of such a joint to form a hydrogen gas running route, the joint itself is small in size, whereby an occupation space for the hydrogen gas running route in a case for the detector can be prevented from becoming large, and a limited space can be effectively utilized to lay a pipeline, so that the portable hydrogen flame ionization gas detector can be prevented from becoming large in size. In addition, leakage of hydrogen gas can be surely prevented, so that there is no risk of causing firing, explosion or the like, and so the detector can be provided as one having extremely high safety.

BRIEF DESCRIPTION OF THE DRAWINGS

The above and other objects, features and advantages of the present invention will become apparent from the following description and the appended claims, taken in conjunction with the accompanying drawings, in which:

DETAILED DESCRIPTION OF THE PREFERRED EMBODIMENTS

The present invention will hereinafter be described with reference to the drawings.

Figure 1:
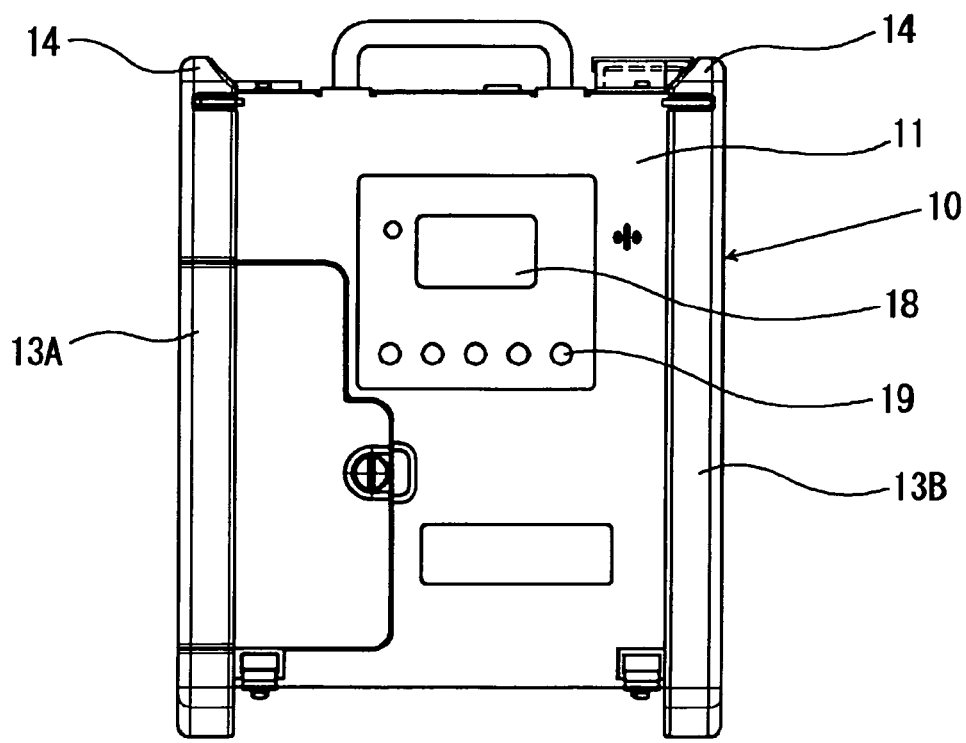
FIG. 1 is a front view illustrating an appearance of a gas detector body in an example of the construction of a portable hydrogen flame ionization gas detector according to the present invention.
Figure 2:
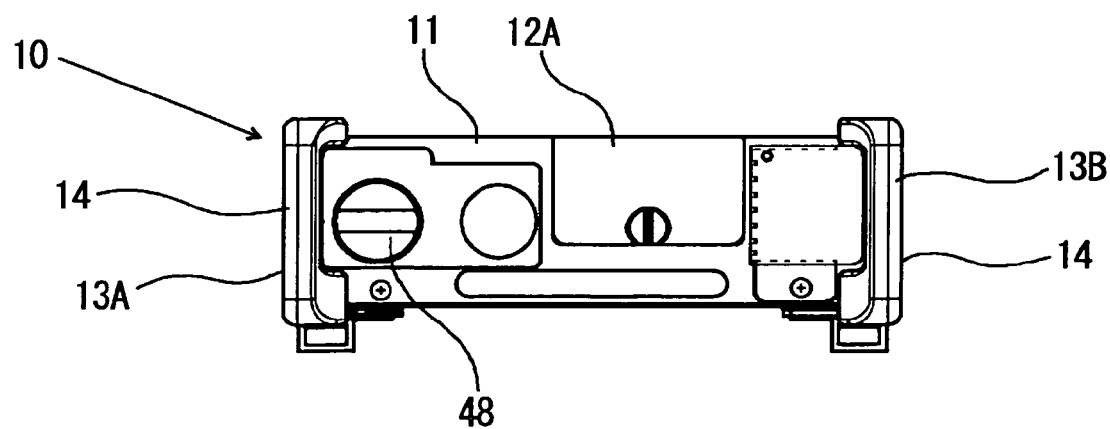
FIG. 2 is a top view of the gas detector body shown in FIG. 1.
Figure 3:
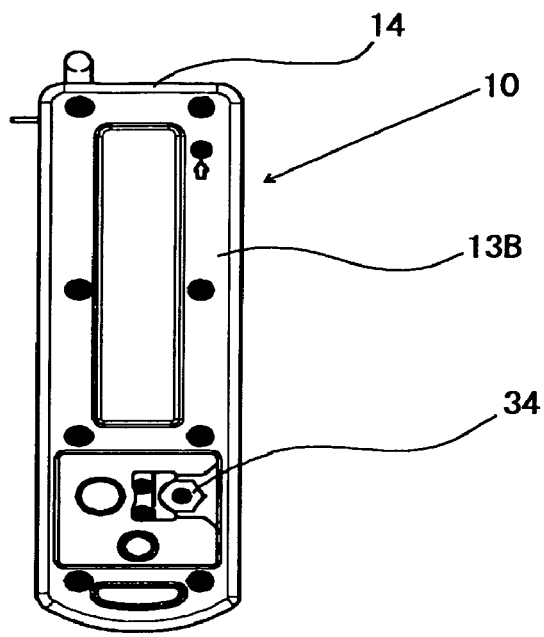
FIG. 3 is a right-hand side elevation of the gas detector body shown in FIG. 1.
Figure 4:
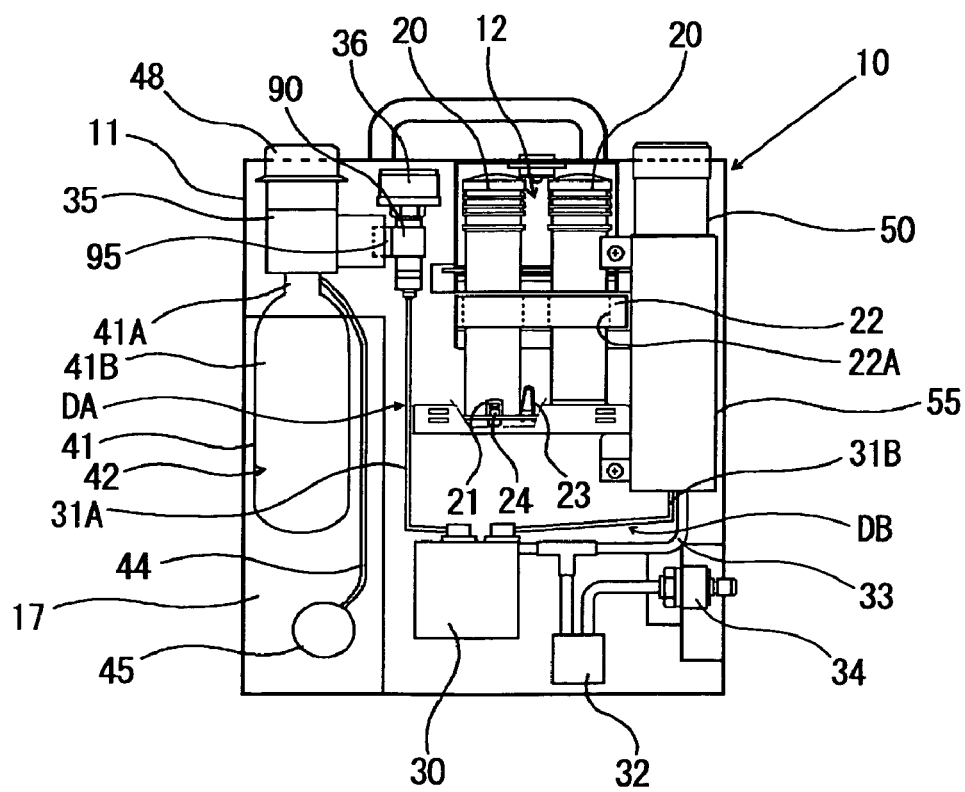
FIG. 4 schematically illustrates the construction of the interior of the gas detector body shown in FIG. 1.

FIG. 1 is a front view illustrating an appearance of a gas detector body in an example of the construction of a portable hydrogen flame ionization gas detector according to the present invention, FIG. 2 is a top view of the gas detector body shown in FIG. 1, FIG. 3 is a right-hand side elevation of the gas detector body shown in FIG. 1, and FIG. 4 schematically illustrates the construction of the interior of the gas detector body shown in FIG. 1. The direction defined in the present description is hereinafter based on a state a standing person carries the gas detector body on his back.

The gas detector body 10 is equipped with a thin-wall box case 11 that can be carried on a person's back. On both sides of this case 11, are provided sidewalls 13A and 13B each composed of a plate-like elastic cover with a metal plate embedded therein.

A display part 18 and an operating part 19 are provided on an upper portion of the case 11 in its front.

A tongue-like piece 14 projecting inward in a crosswise direction facing a side edge portion of an upper plate of the case is provided at an upper end portion of each of the sidewalls 13A and 13B, which are fitted to the case 11 by engaging the tongue-like pieces 14 with the side edge portions in the upper plate of the case 11.

In an upper portion in the interior of the case 11, is formed a battery chamber in which two rod-like rechargeable batteries 20 are arranged side by side in such a manner that each of them extends in a vertical direction. A control part 55 equipped with a signal processing circuit board and a power supplying circuit board, and a hydrogen flame ionization sensor part (hereinafter referred to as "sensor part") 50 are arranged on one side (right side in FIG. 4) of the battery chamber 12, and a hydrogen gas bomb charging chamber 17, in which a hydrogen gas bomb that is a hydrogen gas supplying means for supplying hydrogen gas that is combustion gas to the sensor part 50 is charged, is formed on the other side (left side in FIG. 4) of the battery chamber 12.

In a lower portion in the interior of the case 11, are arranged a flow rate controlling valve 30 for controlling the supply rate of the hydrogen gas and a sample gas sucking pump 32.

The flow rate controlling valve 30 is connected to a gas bomb body 42 in the hydrogen gas bomb through a hydrogen gas running route-forming member 31A extending in a vertical direction in parallel with the gas bomb body 42 and connected to the sensor part 50 through a hydrogen gas running route-forming member 31B extending outward in a crosswise direction toward the sidewall of the case 11 and extending upward from a lower position under the sensor part 50.

The sample gas sucking pump 32 is connected to a connector part 34 for introducing a sample gas, which is provided on one side of the gas detector body 10, and connected to the sensor part 50 through a sample gas supply pipe 33.

The gas detector body 10 is so constructed that the hydrogen gas, which is combustion gas, and the sample gas are supplied to the sensor part 50 in a state separated from each other.

As the rechargeable buttery 20, is used a battery (Type "VP110", manufactured by BLACK & DECKER Co.), whose battery voltage is DC 3.6 V. This battery has a feeding terminal 21 in an inward recessed form at its lower end surface.

Each of the rechargeable butteries 20 is fitted in the battery chamber 12 by being inserted from above in a state that an upper portion of the battery chamber 12 has been opened by pivoting a battery chamber covering lid 12A having bending part extending from the upper surface of the case 11 and bending continuously to a backside thereof.

More specifically, each of the rechargeable batteries 20 is inserted into a battery inserting guide hole 22A in a guide plate 22 for battery insertion to be guided to a negative armature terminal 23, the lower end of which has a function as an elastic guide member, and a positive projecting terminal 24 provided protrudently at a lower end surface of the battery chamber 12 is fitted into the feeding terminal 21 located at the lower end surface of the rechargeable battery 20 in a state that the battery has been pressed on one side by this negative armature terminal 23, whereby the battery is fitted in.

The hydrogen gas bomb is made up by the gas bomb body 42 and a cap 45 for protecting a hydrogen gas ejecting part in the gas bomb body 42.

The gas bomb body 42 is equipped with a pressure container 41 composed of a cylindrical portion forming a neck portion 41A and a closed-end cylindrical portion continuing to the neck portion 41A and forming a body portion 41B having a larger diameter than the neck portion 41A and is made up by integrally fitting the hydrogen gas ejecting part, which is equipped with a valve mechanism for hydrogen gas supply for turning on and off the supply of hydrogen gas by opening and closing a gas conduit for hydrogen gas supply, into the neck portion 41A of the pressure container 41 by screwing the hydrogen gas ejecting part into, for example, a thread groove formed in an internal peripheral surface of the neck portion 41A.

Into the interior of the pressure container 41, is charged, for example, a powdery (particulate) hydrogen-absorbing alloy (not illustrated) that is a hydrogen gas supply source, and the hydrogen gas pressure within the gas bomb body 42 is controlled to, for example, about 1 MPa under ordinary conditions, namely, an ordinary-temperature and ordinary-pressure environment.

This hydrogen gas bomb is in a state that a functional part for opening and closing the gas conduit for hydrogen gas supply has been housed in the neck portion 41A of the pressure container 41, whereby the valve mechanism for hydrogen gas supply is sufficiently protected to achieve high explosion-proofness, so that there is little risk of causing firing, explosion or the like, and so high safety is achieved.

The cap 45 for protecting the hydrogen gas ejecting part is connected to the neck portion 41A of the pressure container 41 in this gas bomb body 42 through a deformable connecting member 44 when the gas bomb body 42 is not charged in the chamber 17, and is held by a cap holding part (not illustrated) provided in the interior of the case 11.

In this gas detector body 10, is arranged a pressure controller 35 for reducing the pressure of hydrogen gas of a high-pressure state of about 1 MPa ejected from the gas bomb body 42, and supplying it in a state of pressure of, for example, 0.05 to 0.3 MPa.

A secondary pressure gauge 36 is connected to an outlet portion of the pressure controller 35 to monitor a pressure of the gas supplied to the hydrogen gas sensor part 50. The opening degree of the flow rate controlling valve 30 is controlled on the basis of the result of this monitoring.

In FIGS. 2 and 4, reference numeral 48 indicates a hydrogen gas-supplying valve mechanism opening and closing knob for opening and closing the hydrogen gas-supplying valve mechanism, which is fitted integrally with the gas bomb body 42. This hydrogen gas-supplying valve mechanism opening and closing knob 48 is pushed and rotated by an inspector or user, whereby the hydrogen gas-supplying valve mechanism is made an opened state to eject hydrogen gas from the gas bomb body 42.

In this gas detector, is formed a hydrogen gas running route comprising a hydrogen gas running route DA extending from the pressure controller 35 to the flow rate controlling valve 30 on the side of the hydrogen gas supply source, and a hydrogen gas running route DB extending from the flow rate controlling valve 30 to the sensor part 50 on the side of the sensor part.

The hydrogen gas running route DA on the side of the hydrogen gas supply source is formed by joining one hydrogen gas running route-forming member 95 extending from the pressure controller 35, and the another hydrogen gas running route-forming member 31A one end of which is connected to the flow rate controlling valve 30, to each other, by means of a specific joint (hereinafter referred to as "joint" merely) 90 for joining hydrogen gas running route-forming members, which will be described subsequently.

Figure 5:
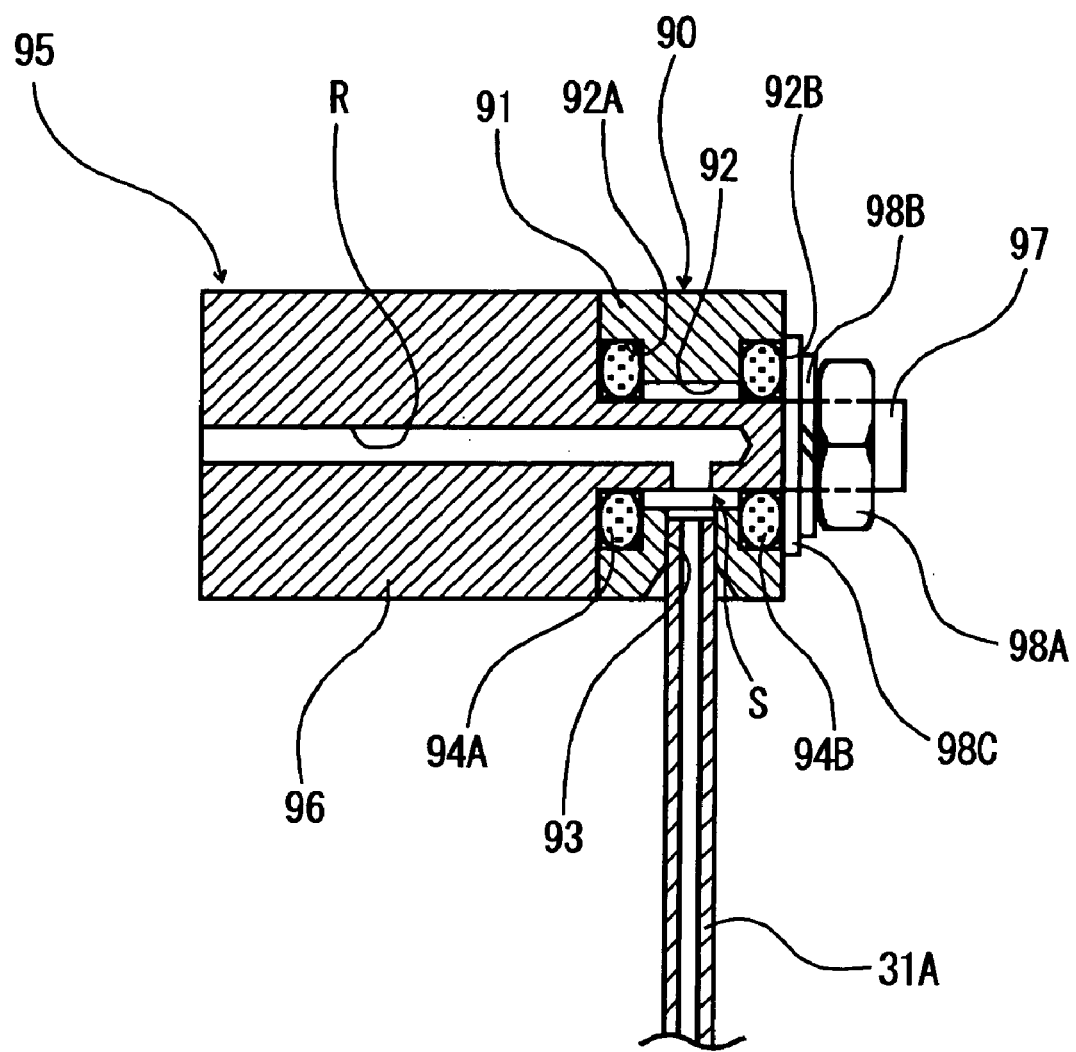
FIG. 5 is a cross-sectional view illustrating an example of the construction of a joint according to the present invention for joining hydrogen gas running route-forming members in a state that the hydrogen gas running route-forming members have been joined.

The joint 90 has a cylindrical metallic base 91 formed by, for example, a brass as illustrated in FIG. 5, and is fabricated by arranging ring-like sealing members, for example, O-rings 94A and 94B, composed of an elastic material at recessed portions 92A and 92B formed at both end opening edges in a central through-hole 92 of the metallic base 91.

A side hole 93 extending from an internal space of the central through-hole 92 toward outside in a radial direction through a peripheral wall and opened at an external peripheral surface of the base is formed in the vicinity of the central portion in an axial direction of the metallic base 91, and one hydrogen gas running route-forming member 95 and the another hydrogen gas running route-forming member 31A are joined, whereby a space S for ejection of hydrogen gas is formed by the internal space of the central through-hole 92. Incidentally, a gas conduit, to which the secondary pressure gauge 36 is connected, is omitted for the sake of convenience in FIG. 5.

In this embodiment, said one hydrogen gas running route-forming member 95 is composed of a large-diameter rod portion 96 connected to the pressure controller 35 at its one end and a small-diameter rod portion 97 continuing to its another end of the large-diameter rod portion 96 is used.

A gas conduit R in said one hydrogen gas running route-forming member 95 extends through the large-diameter rod portion 96 to in the vicinity of the central part in an axial direction of the small-diameter rod portion 97, and extends toward outside in a radial direction of the small-diameter rod portion 97 through the wall thereof in a state that a gas ejecting opening is opened at a peripheral surface of the small-diameter rod portion 97.

The large-diameter rod portion 96 has an outer diameter size equivalent to, for example, the metallic base 91 in the joint 90, and a fitting part (not illustrated) is formed in an external peripheral surface of a proximal end-side portion in an axial direction, an end portion at left in FIG. 5, so as to be screwed into the pressure controller 35 to be connected thereof.

The small-diameter rod portion 97 has an outer diameter size smaller than the opening diameter size or inner diameter size of the central through-hole 92 of the metallic base 91 in the joint 90 and is greater in axial length than the metallic base 91, and a screw thread part (not illustrated), on which a fastening member is screwed, is formed in an external peripheral surface of a tip portion thereof.

Said one hydrogen gas running route-forming member 95 is formed by, for example, a brass or a stainless steel.

Said one hydrogen gas running route-forming member 95 having such a structure is joined to the joint 90 in the following manner. Namely, the small-diameter rod portion 97 is inserted into the central through-hole 92 of the metallic base 91 through the O-ring 94A in a state that the tip portion thereof extends protrudently from the other end of the metallic base 91. In this state, a nut 98A which is the fastening member, is screwed on the screw thread part in the tip portion of the small-diameter rod portion 97 with, for example, a flat washer 98C and a spring washer 98B arranged therebetween, and the nut 98A is fastened at a prescribed rate of fastening, whereby said one hydrogen gas running route-forming member 95 is fixed to the joint 90, and the respective O-rings 94A and 94B are squeezed or deformed by the large-diameter rod portion 96 and the flat washer 98C therebetween to gastightly seal the space S for ejection of hydrogen gas, while said one hydrogen gas running route-forming member 95 is joined to the joint 90 removably.

The another hydrogen gas running route-forming member 31A is inserted into the side hole 93 formed through a peripheral wall of the metallic base 91 in the joint 90 extending in the radial direction thereof and integrally fixed by, for example, brazing so as to open into the internal space of the small-diameter rod portion 97. This hydrogen gas running route-forming member 31A is formed by, for example, a stainless steel.

A specific example of the construction of this joint 90 is illustrated. The size of the outer diameter of the metallic base 91 is 10 mm, and the size of the inner diameter (diameter of the central through-hole 92) thereof is, for example, 4.2 mm; the depth in the axial direction of each of the recessed portions 92A and 92B is, for example, 1.4 mm, and the size of the opening diameter thereof is, for example, 6.8 mm; the thickness of each of the O-rings 94A and 94B is, for example, 1.9 mm, and the inner diameter thereof is, for example, 2.9 mm; and the outer diameter of the small-diameter rod portion 97 in said one hydrogen gas running route-forming member 95 is, for example, 3 mm.

The portable hydrogen flame ionization gas detector of the above-described construction is used by, for example, connecting a sample gas collecting nozzle (not illustrated) for introducing a sample gas (gas to be measured) in a place to be measured to the connector part 34 for introducing the sample gas in the gas detector body 10, carrying the gas detector body 10 on an inspector's back and then bringing the gas detector body 10 to the place to be measured with the inspector in a state that the sample gas collecting nozzle has been held in inspector's hand.

Upon starting gas detection, the hydrogen gas-supplying valve mechanism opening and closing knob 48 is first pushed and rotated by the inspector, whereby the hydrogen gas-supplying valve mechanism is made an opened state to supply hydrogen gas at a prescribed supply rate to the sensor part 50 through the hydrogen gas running route-forming members 31A and 31B, and a power switch of the gas detector body 10 is turned on, whereby a sample gas is sucked by the sample gas sucking pump 32 to supply the sample gas at a prescribed supply rate to the sensor part 50.

In the sensor part 50, the hydrogen gas supplied from the gas bomb body 42 is fired to generate a hydrogen flame, and in this state, the sample gas supplied in a state separated from the hydrogen gas is brought into contact with the hydrogen flame, whereby hydrocarbons contained in the sample gas are thermally decomposed to detect a quantity of a positive ion generated thereby as a current value. On the basis of the detected result, a concentration of the hydrocarbon gas contained in the sample gas is detected, and the result is displayed on the display part 18.

As described above, in the joint 90 of the above-described construction, the fastening member including the nut 98A is screwed into the tip portion of the small-diameter rod portion 97 in the one hydrogen gas running route-forming member 95 in a state that the small-diameter rod portion 97 has been inserted into the central through-hole of the O-ring 94A, the central through-hole 92 of the metallic base 91 and the central through-hole of the O-ring 94B, whereby said one hydrogen gas running route-forming member 95 is fixed in a state brought into no direct contact with the inner wall of the metallic base 91, which forms the space S for ejection of hydrogen gas in the joint 90. Further, the nut 98A is fastened at a prescribed rate of fastening, whereby said one hydrogen gas running route-forming member 95 is fixed to the joint 90 in a state the O-rings 94A and 94B have been squeezed or deformed by the large-diameter rod portion 96 and the flat washer 98C so that said one hydrogen gas running route-forming member 95 and the metallic base 91 are gastightly sealed at the opening edges of the space S for ejection of hydrogen gas. At the same time, the another hydrogen gas running route-forming member 31A is integrally fixed and joined to the joint.

As the hydrogen gas running route-forming members are joined by such a joining manner, the joint 90 of the above-described construction according to the present invention can surely prevent the hydrogen gas from leaking from the joined portion, and moreover the joint 90 itself can be fabricated in a small size because it has an extremely simple structure that the O-rings 94A and 94B are arranged at the opening edges of the metallic base 91.

According to the portable hydrogen flame ionization gas detector of the present invention, which makes good use of such a joint 90 to form a hydrogen gas running route, the joint 90 itself may be thus small in size, whereby an occupation space for the hydrogen gas running route in a case 11 can be prevented from becoming large, and a limited space can be effectively utilized to lay the pipeline, so that the portable hydrogen flame ionization gas detector can be prevented from becoming large in size. In addition, leakage of hydrogen gas can be surely prevented, so that there is no risk of causing firing, explosion or the like, and so the detector can be provided as one having extremely high safety.

While a preferred embodiment of the present invention have been described above, the present invention is not limited to the embodiment described above, and various changes and modifications may be added thereto.

For example, a manner for joining said one hydrogen gas running route-forming member to the joint is not limited to such a manner as described above, and any manner may also be employed so far as the hydrogen gas running route-forming member can be fixed in a state brought into no direct contact with the joint, and a ring-like sealing member or members can be uniformly pressed in an axial direction.

More specifically, for example, the joint may be so fabricated that the metallic base has a structure that only one end of an internal space is opened, and an engaging member which engages with a part to be engaged formed in an external peripheral surface of the large-diameter rod portion in said one hydrogen gas running route-forming member, the small-diameter rod portion of said one hydrogen gas running route-forming member is inserted into the internal space forming the space for ejection of hydrogen gas through an O-ring, the O-ring is squeezed or deformed by the large-diameter rod portion, thereby gastightly sealing the space for ejection of hydrogen gas, and in this state, the engaging member is engaged with the part to be engaged in the external peripheral surface of the large-diameter rod portion, thereby achieving the juncture between said one hydrogen gas running route-forming member and the joint.

For example, the joint may also be so fabricated that a base having a structure that only one end of an internal space is opened is used as the metallic base, a straight pipe member is used as said one hydrogen gas running route-forming member, for example, a cap member fitted on an external peripheral surface of the metallic base is provided in a state the hydrogen gas running route-forming member is rotatably pivoted, and the cap member is, for example, screwed on the external peripheral surface of the metallic base, whereby the pipe member is fixed to the joint, and a sealing member is squeezed or deformed by an internal surface of the cap member to form a gastightly sealed structure, thereby achieving the juncture between said one hydrogen gas running route-forming member and the joint.

In the joint according to the present invention for joining hydrogen gas running route-forming members, no particular limitation is imposed on the degree of inclination of the joining direction of the another hydrogen gas running route-forming member, i.e., the axial direction of the another hydrogen gas running route-forming member to the axial direction of the metallic base, and the inclination may be suitably designed or changed according to a pipeline structure to be formed.

The joint according to the present invention for joining hydrogen gas running route-forming members may be applied to not only hydrogen flame ionization gas detectors, but also instruments in which a hydrogen gas running route is required, particularly, those of a small size.

In the potable hydrogen flame ionization gas detector according to the present invention, may be provided an alarm announcing mechanism for announcing that a hydrogen flame is quenched during measurement or that an atmosphere in a measured place is in a dangerous state.

The potable hydrogen flame ionization gas detector according to the present invention may be so constructed that hydrogen gas and a sample gas are supplied to a gas supplying part in a state separated from each other as above embodiment, or both gasses are supplied to the gas supplying part in a mixed state.

In the above-described embodiment, description has been given as to the case where the gas detector body is carried on an inspector's back to use the gas detector. However, the gas detector may be constructed or used in a state that the gas detector body has been carried on an inspector's shoulder by a proper fitting device, or may be used in such a manner that a handbarrow for installing the gas detector body is used to travel it on the ground.

What is claimed is:

1. A portable hydrogen flame ionization gas detector including a joint for joining hydrogen gas running route-forming members to form a hydrogen gas running route, wherein at least one of the hydrogen gas running route-forming members is removably joined to the joint, the joint comprising:

a metallic base having an internal space forming a space for ejection of hydrogen gas, wherein at least one end of the metallic base is opened, and at least one ring-like sealing member which comprises an elastic material and which is arranged at an opening edge of the metallic base, wherein a first, removably joined hydrogen gas running route-forming member fixed in a state inserted into a central through-hole of the sealing member and the internal space in such a manner that a hydrogen gas ejecting opening is located within the space for ejection of hydrogen gas formed with the internal space, and the at least one sealing member is squeezed, whereby said first hydrogen gas running route-forming member is joined to the joint, and another wherein a second hydrogen gas running route-forming member is joined to open into the space for ejection of hydrogen gas.

2. The portable hydrogen flame ionization gas detector according to claim 1, wherein said first hydrogen gas running route-forming member is joined such that no contact is made with an inner wall of the internal space in the metallic base.

3. The portable hydrogen flame ionization gas detector according to claim 1, wherein the second hydrogen gas running route-forming member is integrally fixed and joined to the metallic base.

4. The portable hydrogen flame ionization gas detector according to claim 3, wherein the second hydrogen gas running route-forming member is fixed through a peripheral wall of the metallic base.

5. The portable hydrogen flame ionization gas detector according to claim 1, wherein the metallic base is cylindrical, and sealing members are arranged at opening edges located at both ends of the metallic base, wherein said first hydrogen gas running route-forming member comprises a large-diameter rod portion and a small-diameter rod portion continuing to an end of the large-diameter rod portion, in which a gas conduit with a gas ejecting opening opened through a peripheral wall of the small-diameter rod portion is formed, and wherein said first hydrogen gas running route-forming member is inserted and arranged into the internal space for forming the space for ejection of hydrogen gas of the metallic base such that a tip portion of the small-diameter rod portion is projected outside the joint, and a fastening member is screwed on the tip portion, whereby said first hydrogen gas running route-forming member is fixed such that the sealing members are squeezed.

6. The portable hydrogen flame ionization gas detector according to claim 5, wherein the second hydrogen gas running route-forming member is integrally fixed and joined to the metallic base.

7. The portable hydrogen flame ionization gas detector according to claim 5, wherein the second hydrogen gas running route-forming member is fixed through a peripheral wall of the metallic base.

8. The portable hydrogen flame ionization gas detector according to claim 2, wherein the second hydrogen gas running route-forming member is integrally fixed and joined to the metallic base.

9. The portable hydrogen flame ionization gas detector according to claim 8, wherein the second hydrogen gas running route-forming member is fixed through a peripheral wall of the metallic base.

10. The portable hydrogen flame ionization gas detector according to claim 2,
wherein the metallic base is cylindrical, and sealing members are arranged at opening edges located at both ends of the metallic base,
wherein said first hydrogen gas running route-forming member comprises a large-diameter rod portion and a small-diameter rod portion continuing to an end of the large-diameter rod portion, in which a gas conduit with a gas ejecting opening opened through a peripheral wall of the small-diameter rod portion is formed, and
wherein said first hydrogen gas running route-forming member is inserted and arranged into the internal space for forming the space for ejection of hydrogen gas of the metallic base such that a tip portion of the small-diameter rod portion is projected outside of the joint, and a fastening member is screwed on the tip portion, whereby said first hydrogen gas running route-forming member is fixed such that the sealing members are squeezed.

11. The portable hydrogen flame ionization gas detector according to claim 10, wherein the second hydrogen gas running route-forming member is integrally fixed and joined to the metallic base.

12. The portable hydrogen flame ionization gas detector according to claim 10, wherein the second hydrogen gas running route-forming member is fixed through a peripheral wall of the metallic base.

* * * * *